(12) United States Patent
Yamada et al.

(10) Patent No.: US 9,322,708 B2
(45) Date of Patent: Apr. 26, 2016

(54) OPTICAL DEVICE, DETECTION APPARATUS, ELECTRONIC APPARATUS, AND METHOD FOR PRODUCING OPTICAL DEVICE

(71) Applicant: Seiko Epson Corporation, Tokyo (JP)

(72) Inventors: Akiko Yamada, Suwa (JP); Kohei Yamada, Suwa (JP)

(73) Assignee: Seiko Epson Corporation (JP)

( * ) Notice: Subject to any disclaimer, the term of this patent is extended or adjusted under 35 U.S.C. 154(b) by 138 days.

(21) Appl. No.: 14/104,366

(22) Filed: Dec. 12, 2013

(65) Prior Publication Data

US 2014/0166863 A1 Jun. 19, 2014

(30) Foreign Application Priority Data

Dec. 13, 2012 (JP) .................................. 2012-272042

(51) Int. Cl.
*G01N 21/00* (2006.01)
*G01J 1/42* (2006.01)
*B82Y 15/00* (2011.01)
*G01N 21/65* (2006.01)

(52) U.S. Cl.
CPC . *G01J 1/42* (2013.01); *B82Y 15/00* (2013.01); *G01N 21/65* (2013.01); *G01N 21/658* (2013.01); *Y10T 428/256* (2015.01); *Y10T 428/31678* (2015.04)

(58) Field of Classification Search
CPC .......... G01J 1/42; G01N 21/65; G01N 21/658
See application file for complete search history.

(56) References Cited

U.S. PATENT DOCUMENTS 5,225,274 A 7/1993 Ogawa et al.
8,003,408 B2 * 8/2011 Zhang et al. .................. 436/525

FOREIGN PATENT DOCUMENTS

| JP | 05-096679 | 4/1993 |
| JP | 2008-177283 A | 7/2008 |
| JP | 2009-222401 A | 10/2009 |
| JP | 2013-096939 A | 5/2013 |

OTHER PUBLICATIONS

Olga Lyandres et al., "Real-Time Glucose Sensing by Surface-Enhanced Raman Spectroscopy in Bovine Plasma Facilitated by a Mixed Decanethiol/Mercaptohexanol Partition Layer", Chemistry Department and Department of Biomedical Engineering, Northwestern University, Analytical Chemstry, vol. 77, No. 19, Oct. 1, 2005, pp. 6134-6139.
Peter Freunscht et al., "Surface-Enhanced Raman Spectroscopy of Trans-Stilbene Adsorbed on Platinum- or Self-Assembled Monolayer-Modified Silver Silm Over Nanosphere Surfaces", Department of Chemistry, Northwestern University, Chemical Physics Letters, 281, Oct. 15, 1997, pp. 372-378.

* cited by examiner

*Primary Examiner* — Tony Ko
(74) *Attorney, Agent, or Firm* — Harness, Dickey & Pierce, P.L.C.

(57) ABSTRACT

An optical device includes: a substrate having a dielectric layer and a plurality of metal particles; and an organic molecular layer formed by self-assembly on at least either the surface of the dielectric layer or the surfaces of the metal particles. In the organic molecular layer, a first organic molecule and a second organic molecule are alternately arranged in a first direction, and the chain length of an organic group of the first organic molecule and the chain length of an organic group of the second organic molecule are different from each other.

18 Claims, 13 Drawing Sheets

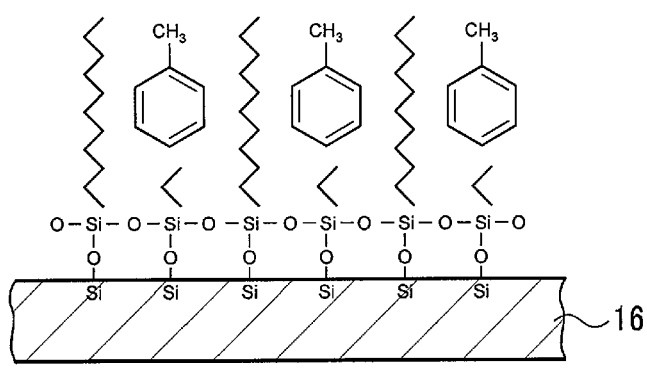 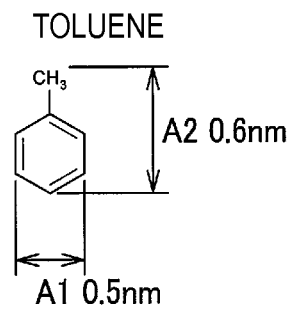
FIG.12A  FIG.12B
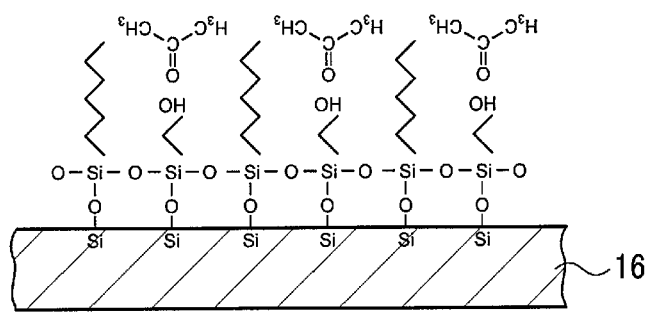 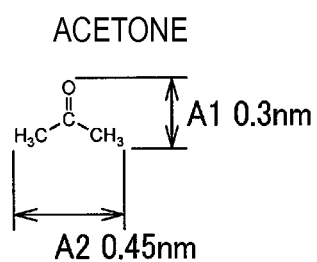
FIG.13A  FIG.13B
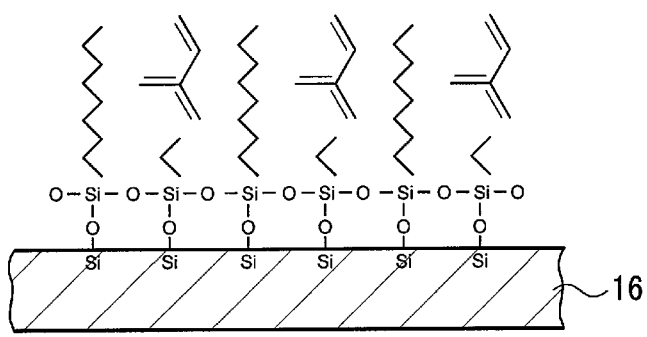 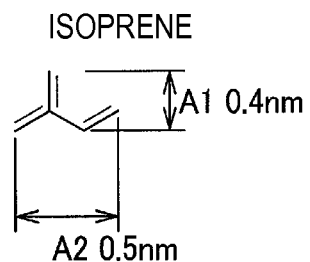
FIG.14A  FIG.14B

| TYPE OF GROUP Y1 | CHAIN LENGTH OF GROUP Y1 ×2 [nm] | w [nm] |
|---|---|---|
| Cl | 0.22 | 0.14 |
| OCH$_3$ | 0.41 | 0.37 |
| OCH$_2$CH$_3$ | 0.66 | 0.60 |

FIG.15

|  | EXAMPLE 1 | EXAMPLE 2 | EXAMPLE 3 |
|---|---|---|---|
| NUMBER OF CARBON ATOMS OF R1 | 18 | 10 | 6 |
| CHAIN LENGTH r1 OF R1 | 2.13 nm | 1.13 nm | 0.63 nm |
| NUMBER OF CARBON ATOMS OF R2 | 3 | 3 | 3 |
| CHAIN LENGTH r2 OF R2 | 0.25 nm | 0.25 nm | 0.25 nm |
| LENGTH OF r | 1.88 nm | 0.88 nm | 0.38 nm |

FIG.16

|  | BEFORE FORMING SAM | FORMING ONLY SAM1 | FORMING SAM1 AND SAM2 (EMBODIMENT OF THE INVENTION) |
|---|---|---|---|
| ACETONE 787cm$^{-1}$ | 30 | 400 | 1800 |

FIG.17 ns, in the organic
molecular layer, a first organic molecule and a second organic
molecule are alternately arranged in a first direction, and the
chain length of an organic group of the first organic molecule
and the chain length of an organic group of the second organic
molecule are different from each other.
OPTICAL DEVICE, DETECTION APPARATUS, ELECTRONIC APPARATUS, AND METHOD FOR PRODUCING OPTICAL DEVICE

BACKGROUND

1. Technical Field

The present invention relates to an optical device, a detection apparatus, an electronic apparatus, and a method for producing an optical device.

2. Related Art

Recently, the demand for a sensor chip to be used for medical diagnoses, tests for foods and beverages, etc. has been increasing, and the development of a highly sensitive and small sensor chip has been demanded. In order to respond to such a demand, various types of sensor chips such as electrochemical sensor chips have been studied. Among these, for the reasons that integration is possible, the cost is low, measurement can be performed in any environment, etc., sensor chips using a spectroscopic analysis utilizing surface plasmon resonance (SPR), particularly, surface-enhanced Raman scattering (SERS) have drawn increasing attention.

Here, the term "surface plasmon" refers to an oscillation mode of an electron wave that is coupled to light depending on boundary conditions specific to a surface. As a method for exciting surface plasmons, there is a method in which a diffraction grating is imprinted on a metal surface to couple light to plasmons or a method in which an evanescent wave is used. For example, as a sensor utilizing SPR, a sensor configured to include a total reflection prism and a metal layer which comes into contact with a target substance formed on the surface of the prism is known. According to such a configuration, whether or not a target substance is adsorbed, for example, whether or not an antigen is adsorbed in an antigen-antibody reaction, or the like is detected.

However, while propagating surface plasmons exist on a metal surface, localized surface plasmons exist on a metal fine particle. It is known that when the localized surface plasmons, i.e., the surface plasmons localized on the metal microstructure on the surface are excited, a significantly enhanced electric field is generated.

It is also known that when an enhanced electric field formed by localized surface plasmon resonance (LSPR) using metal nanoparticles is irradiated with a Raman scattered light, the Raman scattered light is enhanced by surface-enhanced Raman scattering phenomenon, and therefore, a sensor (detection apparatus) with high sensitivity has been proposed. By using this principle, it becomes possible to detect a small amount of various substances.

An enhanced electric field is large around metal particles, particularly in a gap between adjacent metal particles, and therefore, it is necessary to retain a target molecule in a fluid sample in the gap between metal particles. For example, in Patent Literature 1 (JP-A-2009-222401) or Non-Patent Literature 1 (P. Freunscht et al., "Surface-enhanced Raman spectroscopy of trans-stilbene adsorbed on platinum or self-assembled monolayer-modified silver film over nanosphere surfaces", Chemical Physics Letters, 281 (1997), 372-378), as schematically shown in FIGS. 1A and 1B, on a metal surface of a sensor substrate 200, a self-assembled monolayer (SAM) film 201 is formed, and a target molecule 202 or 203 is adsorbed thereon, whereby the detection sensitivity of SERS is improved. Further, in Patent Literature 2 (JP-A-2008-177283), by repeating a formation step, a self-assembled monolayer film having few defects is formed.

In Non-Patent Literature 2 (Olga Lyandres et al., "Real-Time Glucose Sensing by Surface-Enhanced Raman Spectroscopy in Bovine Plasma Facilitated by a Mixed Decanethiol/Mercaptohexanol Partition Layer", Anal. Chem., 77 (2005), 6134-6139), as schematically shown in FIG. 2, by forming and mixing two types of SAMs 210 and 211 having an organic group with a different length, a capture space 212 having a hydrophilic group and a hydrophobic group is formed, and a target molecule (glucose) 213 is adsorbed in the capture space 212, whereby the detection sensitivity of SERS is improved.

When one type of SAM 201 is formed, in the case of a large target molecule 202 such as a protein shown in FIG. 1A, there are many adsorption sites between the target molecule 202 and the surface of the SAM 201, and the target molecule 202 is held by multipoint adsorption. On the other hand, in the case where a target molecule 203 shown in FIG. 1B has a low molecular weight (for example, a volatile organic compound (VOC) such as toluene, xylene, acetone, or isoprene), since the molecule is small, the number of adsorption sites is about 1, and therefore, since the adsorption force is small, sufficient detection sensitivity cannot be obtained.

On the other hand, as the method for forming two types of SAMs 210 and 211 shown in FIG. 2, there are the following two methods: one is a method in which a substrate is immersed in a solution obtained by mixing different SAM constituent molecules at a given ratio, whereby two types of SAMs are formed; and the other is a method in which one SAM is formed in advance for a relatively short formation period, and thereafter, the other SAM is formed.

However, the above-described methods have a problem, for example, the same type of SAM molecules aggregate, or an SAM which is easily formed is preferentially formed, and therefore, it is difficult to form the capture space 212 in a regularly arranged pattern as shown in FIG. 2. Further, the size (the width in the arrangement direction) of the capture space 212 as shown in FIG. 2 cannot be controlled.

SUMMARY

An advantage of some aspects of the invention is to provide an optical device, a detection apparatus, an electronic apparatus, and a method for producing an optical device, capable of further improving the detection sensitivity by capturing a substance such as a target molecule in a capture space formed by at least two types of organic molecules.

An advantage of some other aspects of the invention is to provide an optical device, a detection apparatus, an electronic apparatus, and a method for producing an optical device, capable of further improving the detection sensitivity by regularly arranging a capture space matched with the size of a substance such as a target molecule.

(1) An aspect of the invention relates to an optical device including: a substrate having a dielectric layer and metal particles; and an organic molecular layer formed by self-assembly on at least either the surface of the dielectric layer or the surfaces of the metal particles, wherein in the organic molecular layer, a first organic molecule and a second organic molecule are alternately arranged in a first direction, and the chain length of an organic group of the first organic molecule and the chain length of an organic group of the second organic molecule are different from each other.

According to the aspect of the invention, the organic molecular layer is configured such that the first organic molecule and the second organic molecule are alternately arranged in the first direction, in other words, the second organic molecule is arranged between, for example, the two first organic molecules having a long chain length arranged along the first direction. Since the respective chain lengths of the first and second organic groups are different, concave portions are regularly formed due to the chain length difference. The concave portion can be used as a capture region in which a given substance, for example, a target molecule is held by multipoint adsorption.

(2) In one aspect of the invention, in the organic molecular layer, the first organic molecule and the second organic molecule are arranged in a checkered pattern, in other words, the second organic molecule is arranged, for example, between the two first organic molecules having a long chain length arranged along a first direction, and also the second organic molecule is arranged, for example, between the two first organic molecules having a long chain length arranged along a second direction intersecting the first direction.

According to the aspect of the invention, the organic molecular layer is configured such that the first organic molecule and the second organic molecule are in a checkered pattern, in other words, the second organic molecule is arranged between, for example, the two first organic molecules having a long chain length arranged along the first direction, and also the second organic molecule is arranged between, for example, the two first organic molecules having a long chain length arranged along a second direction intersecting the first direction. Since the respective chain lengths of the first and second organic groups are different, concave portions are regularly formed due to the chain length difference. The concave portion can be used as a capture region in which a given substance, for example, a target molecule is held by multipoint adsorption.

(3) In one aspect of the invention, the organic molecular layer has a capture region in which a given substance is captured on the surface thereof, the capture region is defined by a chain length difference between the organic group of the first organic molecule and the organic group of the second organic molecule and the arrangement interval of the first organic molecule having a longer chain length than the second organic molecule, and the self-assembly occurs such that the organic molecular layer, in which the molecules have the same orientation, is formed on the surface by an interaction between the first organic molecule and the second organic molecule chemically adsorbed on the surface in a solution or a vapor.

The capture region having a depth corresponding to the chain length difference between the first organic group and the second organic group and having a width corresponding to the arrangement interval of the first organic molecule having a longer chain length between the first and the second organic molecules is regularly formed. Therefore, the density of the capture region in which a given substance, for example, a target molecule can be held by multipoint adsorption is increased, and a detection signal level for the target molecule or the like can be increased.

(4) In one aspect of the invention, when the chain length difference between the organic group of the first organic molecule and the organic group of the second organic molecule is represented by r, the arrangement interval of the first organic molecule is represented by w, and the lengths of two axes defining the maximum area among the projected areas in three orthogonal axial directions of the target molecule are represented by A1 and A2 (A1≤A2), r, w, A1, and A2 satisfy the following formulae: $A1 < w \le 2 \times A1$; and $A2 \le r \le 2 \times A2$.

According to this configuration, the length A1 of one of the axes defining the maximum projected area of a given substance, for example, a target molecule falls within the width w of the capture region, and the length A2 of the other of the axes defining the maximum projected area of the target molecule falls within the depth r of the capture region, and thus, the target molecule can be adsorbed in the capture region conforming to the size of the target molecule. In particular, in the case where A1<A2, the target molecule can fit in the width w of the capture region in a vertically long state. As a result, it becomes possible to select the target molecule by the capture region. That is, a noise molecule having a size larger than the target molecule is not captured in the capture region. In this manner, since the capture region is not occupied by a noise molecule, the detection signal level for the target molecule can be increased. Further, since the size of the capture region is not excessively increased, the density of the capture region is further increased.

(5) In one aspect of the invention, when the chain length difference between the organic group of the first organic molecule and the organic group of the second organic molecule is represented by r, the arrangement interval of the first organic molecule is represented by w, and the lengths of two axes defining the maximum area among the projected areas in three orthogonal axial directions of the given substance are represented by A1 and A2 (A1≤A2), r, w, A1, and A2 satisfy the following formulae: $A2 < w \le 2 \times A2$; and $A1 \le r \le 2 \times A1$.

According to this configuration, the length A1 of one of the axes defining the maximum projected area of a given substance, for example, a target molecule falls within the depth r of the capture region in a horizontally long state, and the length A2 of the other of the axes defining the maximum projected area of the target molecule falls within the width w of the capture region, and thus, the target molecule can be adsorbed in the capture region conforming to the size of the target molecule. Also in this case, in the same manner as (3), the detection signal level for the target molecule can be increased. However, the density of the capture region is lower than in the case of (3).

(6) In one aspect of the invention, when the length of a first axis connecting two atoms located farthest from each other in the given substance is represented by a1, and the length of a second axis connecting two atoms located farthest from each other in an orthogonal projection of the given substance on a surface orthogonal to the first axis is represented by a2, the length A1 and the length A2 are defined on the basis of the length a1 of the first axis and the length a2 of the second axis, respectively.

According to this configuration, the lengths A1 and A2 can be determined on the basis of the lengths a1 and a2 between atoms in the given substance.

(7) Another aspect of the invention relates to a detection apparatus including: a light source; the optical device according to any of the above (1) to (6), on which a light from the light source is incident; and a light detector which detects a light emitted from the optical device. The detection sensitivity of this detection apparatus is improved by using the above-described optical device.

(8) Still another aspect of the invention relates to an electronic apparatus including: the detection apparatus according to the above (7); a calculation section which calculates health or medical information on the basis of the detection information from the detection apparatus; a storage section which stores the health or medical information; and a display section which displays the health or medical information. This electronic apparatus is useful for medical diagnoses, tests for foods and beverages, etc.

(9) Yet another aspect of the invention relates to a method for producing an optical device including: forming an organic molecular layer on at least either the surface of a dielectric layer or the surfaces of metal particles formed on a substrate by self-assembling a first organic molecule having a first organic group in an arrangement direction so as to maintain a predetermined interval; removing a sterically hindered group in the first organic molecule which regulates the interval by hydrolysis; and forming an organic molecular layer by self-assembling a second organic molecule having a second organic group with a different chain length from the first organic group between the adjacent first organic molecules on the surface.

According to this production method, in the step of self-assembling the first organic molecule, with respect to the adjacent two first organic molecules to be attached to the substrate, the interval in the arrangement direction is regulated by the interference of the sterically hindered groups protruding in the arrangement direction. Therefore, the first organic molecule is regularly arranged. Subsequently, by hydrolyzing the sterically hindered group in the first organic molecule which regulates the arrangement interval in the arrangement direction, the sterically hindered group is replaced by an OH group. Thereafter, between the adjacent two first organic molecules in the arrangement direction, the second organic molecule is self-assembled and attached to the substrate. At this time, the sterically hindered group of the first organic molecule has already been hydrolyzed, and therefore is no longer an obstacle to the second organic molecule entering between the two first organic molecules. In this manner, a capture region having a depth corresponding to the chain length difference between the first organic group and the second organic group and having a width corresponding to the arrangement interval of the first organic molecule is regularly formed.

(10) In one aspect of the invention, when a backbone atom is represented by Si, the first organic group is represented by R1, the sterically hindered group is represented by Y1, and a first functional group to be attached to the substrate is represented by X1, the first organic molecule is represented by the formula (1), and the sterically hindered group Y1 is any of an alkoxy group (having 1 to 10 carbon atoms), a phenoxy group, and a halogen group, and is replaced by an OH group by hydrolysis.

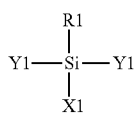
(1)

Here, by adopting any of an alkoxy group (having 1 to 10 carbon atoms), a phenoxy group, and a halogen group as the sterically hindered group Y1, the sterically hindered group Y1 can be replaced by an OH group by hydrolysis. Further, the OH group can form an Si—O bond by a condensation reaction when the group is attached to the second organic molecule.

(11) In one aspect of the invention, when a backbone atom is represented by Si, the second organic group is represented by R2, a second functional group to be attached to the substrate is represented by X2, and the remaining groups are represented by Y2 and Y3, the second organic molecule is represented by the formula (2), and the group Y2 and the group Y3 each are any of an alkoxy group (having 1 to 10 carbon atoms), a phenoxy group, a hydroxy group, and a halogen group.

Each of the group Y2 and the group Y3 can form an Si—O bond by a condensation reaction when the group is linked to the OH group of the first organic molecule.

(12) In one aspect of the invention, the first organic group R1 and the second organic group R2 each have a linear, branched, or cyclic structure having one or more functional groups selected from the group consisting of an alkyl group, a vinyl group, an aryl group, a hydroxy group, an aldehyde group, a carbonyl group, a carboxy group, a nitro group, an amino group, a sulfo group, an ether bond, an ester bond, an amide bond, a cyano group, an imino group, a cycloalkyl group, an alkenyl group, an alkynyl group, an epoxy group, a mercapto group, and a halogen group.

Here, as the first organic group R1 and the second organic group R2, groups having a different chain length are selected from the above-described functional groups. Even in the case of the functional groups of the same type, some functional groups have a different chain length since, for example, the number of carbon atoms is different.

(13) In one aspect of the invention, when the first organic molecule and the second organic molecule are formed on the dielectric layer, the first functional group X1 and the second functional group X2 are each any of an alkoxy group (having 1 to 10 carbon atoms), a phenoxy group, a hydroxy group, and a halogen group.

Each of the first functional group X1 and the second functional group X2 can undergo a condensation reaction when the group is attached to the dielectric layer, whereby the first organic molecule and the second organic molecule can be attached to the dielectric layer.

(14) In one aspect of the invention, when the first organic molecule and the second organic molecule are formed on a plurality of the metal particles, the first functional group X1 and the second functional group X2 are each any of a thiol group, a thioisocyanide group, and an isocyanide group.

If each of the first functional group X1 and the second functional group X2 is a thiol group or a thioisocyanide group, an S-metal bond is formed when the group is attached to the metal particle, and if each of the first functional group X1 and the second functional group X2 is an isocyanide group, an NC-metal bond is formed when the group is attached to the metal particle.

(15) In one aspect of the invention, as the backbone atom, any of Ti, Zr, and Al atoms is used in place of Si.

By selecting the backbone atom, the width of selection of the first and second organic molecules to be used in the production method according to the aspect of the invention is expanded.

BRIEF DESCRIPTION OF THE DRAWINGS

The invention will be described with reference to the accompanying drawings, wherein like numbers reference like elements.

FIGS. 12A and 12B are views showing a capture space conforming to the size of toluene and the size of toluene, respectively.

FIGS. 13A and 13B are views showing a capture space conforming to the size of acetone and the size of acetone, respectively.

FIGS. 14A and 14B are views showing a capture space conforming to the size of isoprene and the size of isoprene, respectively.

FIG. 15 is a table showing the width w of a capture space adjusted by a group Y1 of a first organic molecule.

FIG. 16 is a table showing the depth r of a capture space determined by a chain length difference (r1−r2) in which r1 represents the chain length of a first organic group R1 and r2 represents the chain length of a second organic group R2.

FIG. 17 is a table showing the SERS signal intensity of acetone along with those of Comparative Examples.

DESCRIPTION OF EXEMPLARY EMBODIMENTS

Hereinafter, preferred embodiments of the invention will be described in detail. The embodiments described below do not unduly limit the contents of the invention described in the appended claims, and all of the structures described in the embodiments are not indispensable for the solving means of the invention.

1. Basic Structure of Optical Device

Figure 1A:
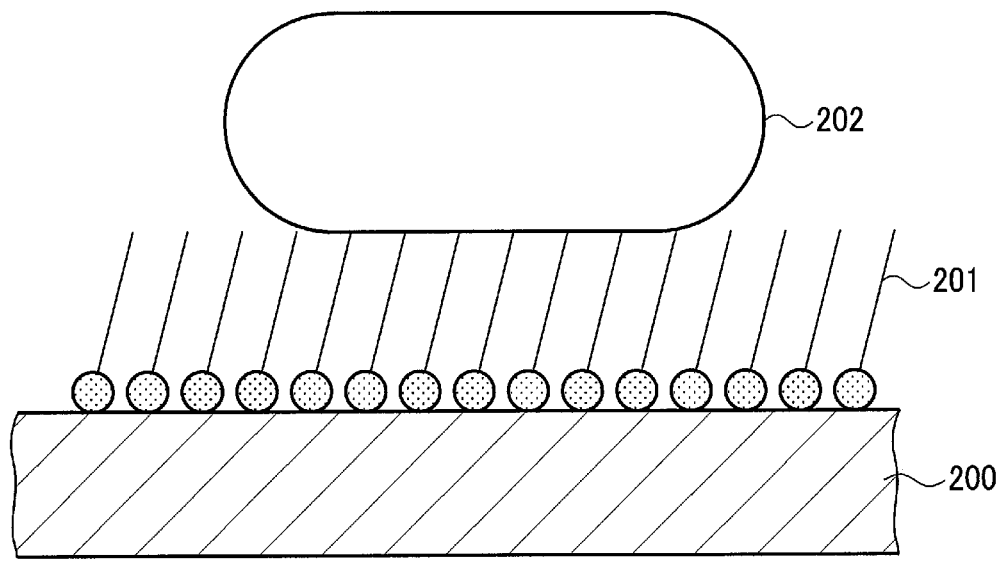
FIGS. 1A and 1B are schematic views each showing an optical device in the related art.
Figure 1B:
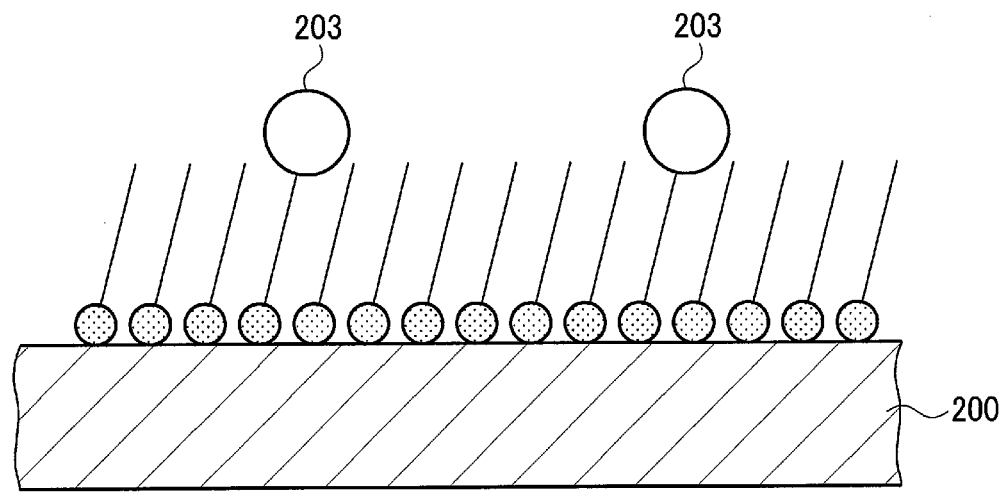
Figure 2:
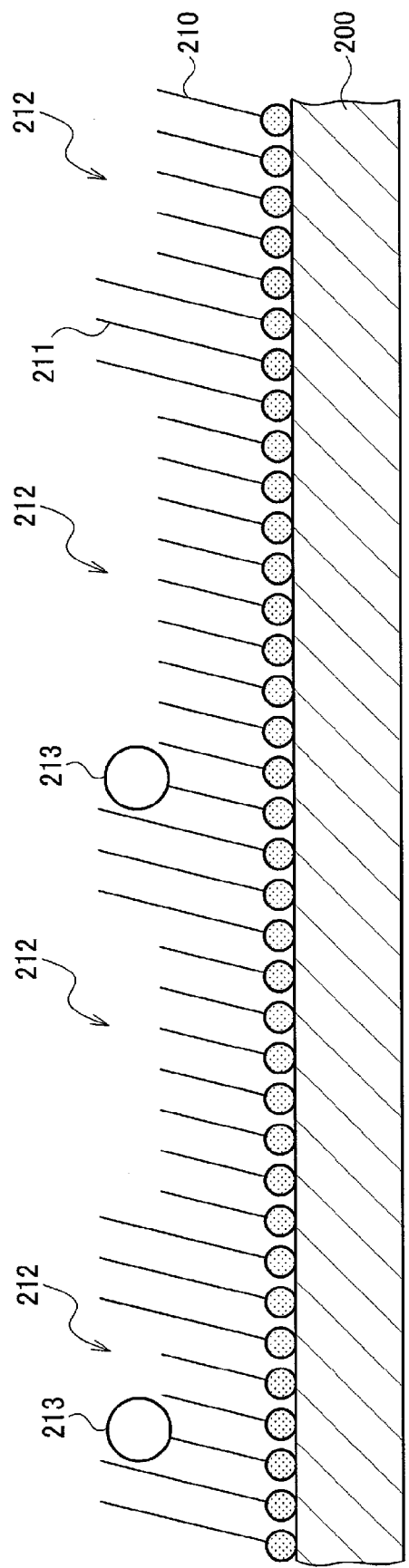
FIG. 2 is a schematic view showing an optical device in the related art different from those shown in FIGS. 1A and 1B.
Figure 3A:
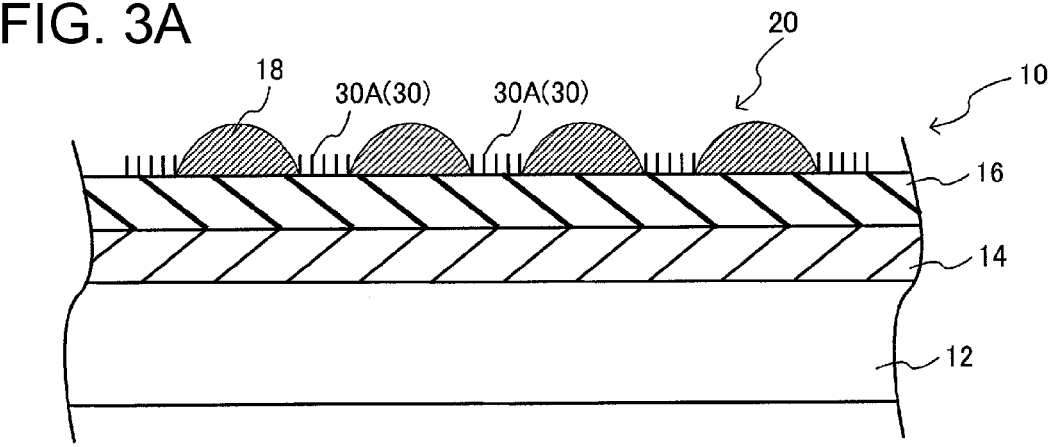
FIGS. 3A to 3C are views each showing an optical device having an organic molecular layer on at least either a dielectric layer or a plurality of metal particles on a substrate.
Figure 3B:
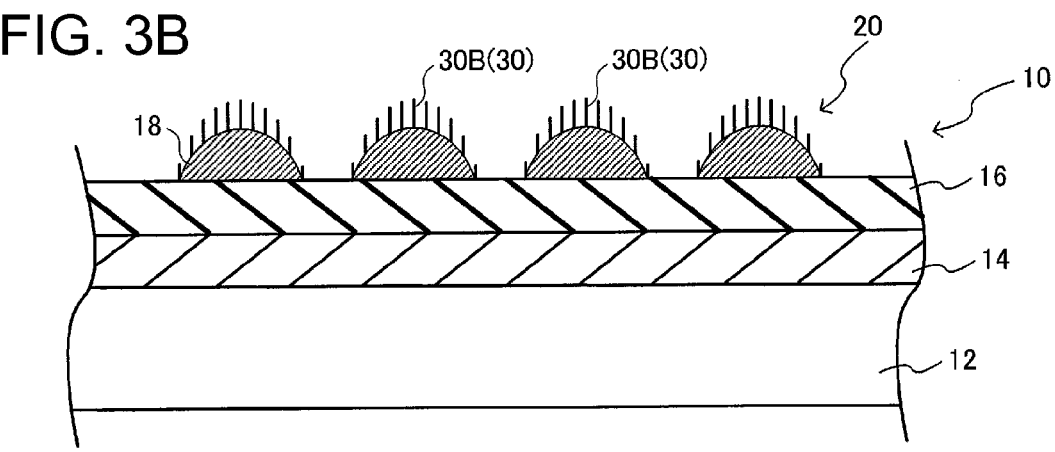
Figure 3C:
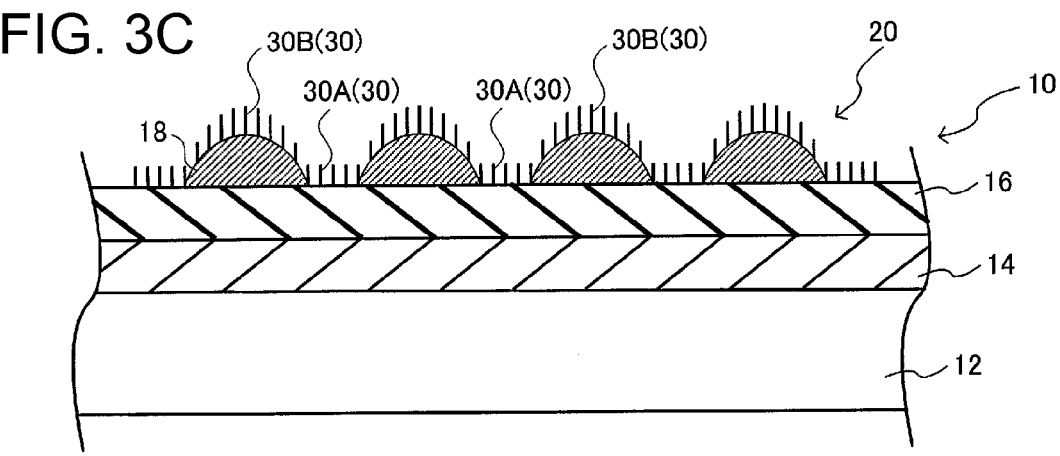

Optical devices 10 shown in FIGS. 3A to 3C each have a dielectric layer 16 on one outermost surface of a substrate 12. The substrate 12 itself may be a dielectric body such as an oxide, and in such a case, the substrate 12 can be formed from glass, mica, $SiO_2$, $SnO_2$, $GeO_2$, $ZrO_2$, $TiO_2$, $Al_2O_3$, PZT, or the like. On the substrate 12 made of a material other than a dielectric body, the above-described dielectric layer 16 may be formed. In this embodiment, for example, a metal (dielectric) layer 14 can be provided between the substrate 12 made of glass and the dielectric layer 16.

On the dielectric layer 16, a metal microstructure 20 composed of a plurality of metal particles 18 is formed. The plurality of metal particles 18 can be arranged at a period P. The period P is not limited to a constant period, and the metal particles 18 may be arranged randomly at a period including a minimum period P. The metal particles 18 may be arranged one-dimensionally or two-dimensionally.

The metal particle 18 is a metal nanoparticle in a nano-order size smaller than the wavelength of an incident light, and has a size (particle diameter) in plan view of 1 to 500 nm. Here, the "incident light" is an excitation light which excites surface plasmons localized on the metal microstructure 20 on the surface. As the metal particle 18, for example, gold (Au), silver (Ag), copper (Cu), aluminum (Al), palladium (Pd), nickel (Ni), platinum (Pt), molybdenum (Mo), chromium (Cr), an alloy thereof, or a composite thereof is used. The metal particle 18 may be formed so as to cover a convex portion of an insulating body (see FIG. 4D).

The metal layer 14 is formed as an enhanced structure of propagating plasmons, and a smooth film, a metallic diffraction grating with periodic irregularities, or the like is suitable. In FIGS. 3A to 3C, an example in which the metal layer 14 made of gold (Au) is formed by a vacuum vapor deposition method or a sputtering method is shown. The thickness of the Au film is preferably from about 10 nm to several tens of micrometers. As the type of the metal, gold (Au), silver (Ag), copper (Cu), aluminum (Al), platinum (Pt), nickel (Ni), palladium (Pd), tungsten (W), rhodium (Rh), ruthenium (Ru), or the like is suitable.

As the dielectric layer 16 formed on the metal layer 14, an oxide such as $SiO_2$, $Al_2O_3$, or $TiO_2$ is suitable, and the thickness thereof is preferably from about 10 nm to 1000 nm.

In this embodiment, the optical device 10 can include an organic molecular layer 30A on the dielectric layer 16 between the adjacent metal particles 18 as shown in FIG. 3A. Alternatively, as shown in FIG. 3B, the optical device 10 can include an organic molecular layer 30B on the metal particles 18. Alternatively, as shown in FIG. 3C, the optical device 10 can include both of the organic molecular layer 30A shown in FIG. 3A and the organic molecular layer 30B shown in FIG. 3B. That is, in this embodiment, an organic molecular layer 30 (30A or 30B) can be formed on at least either the dielectric layer 16 or the plurality of metal particles 18 formed on the surface of the substrate 12. The organic molecular layer 30 is an adsorption layer which bonds (captures) a given substance, for example, a target molecule, and can be formed from, for example, a self-assembled monolayer (SAM) film. Incidentally, in FIGS. 3A to 3C, only a one-dimensional arrangement is shown, however, in fact, a two-dimensional arrangement is adopted.

2. Light Detection Principle

Figure 4A:
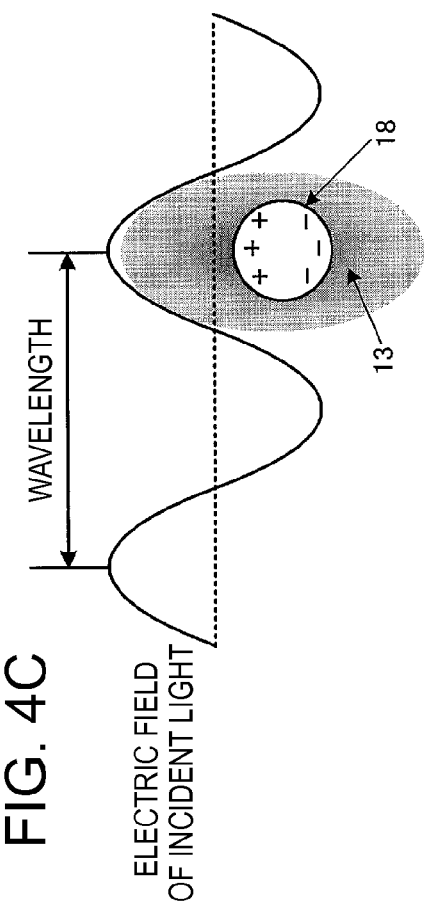
FIGS. 4A to 4D are views for explaining the detection principle of a surface-enhanced Raman scattered light.

With reference to FIGS. 4A to 4D, as one example of detection principle of light reflecting a target molecule, detection principle of a Raman scattered light will be described. As shown in FIG. 4A, a target molecule 1 (see FIG. 4D) which is a detection target to be adsorbed on the optical device 10 is irradiated with an incident light (frequency: ν). In general, most of the incident light is scattered as a Rayleigh scattered light, and the frequency ν or the wavelength of the Rayleigh scattered light does not change from that of the incident light. Part of the incident light is scattered as a Raman scattered light, and the frequency (ν−ν' and ν+ν') or the wavelength of the Raman scattered light reflects the frequency ν' (molecular oscillation) of the target molecule 1. That is, the Raman scattered light is a light reflecting the target molecule 1 to be detected. Part of the incident light allows the target molecule 1 to oscillate and loses energy, but the oscillation energy of the target molecule 1 may be sometimes added to the oscillation energy or the light energy of the Raman scattered light. Such shift in frequency (ν') is called Raman shift.

Figure 4B:
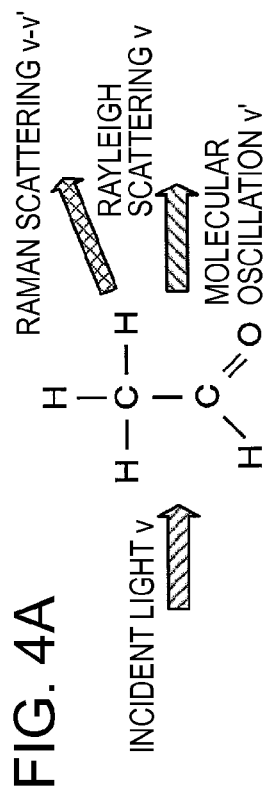

FIG. 4B shows an example of acetaldehyde as a fingerprint spectrum specific to a target molecule. By this fingerprint spectrum, the detected substance can be identified as aldehyde. However, the intensity of the Raman scattered light is very low, and therefore, it is difficult to detect a substance which is present only in a small amount.

Figure 4C:
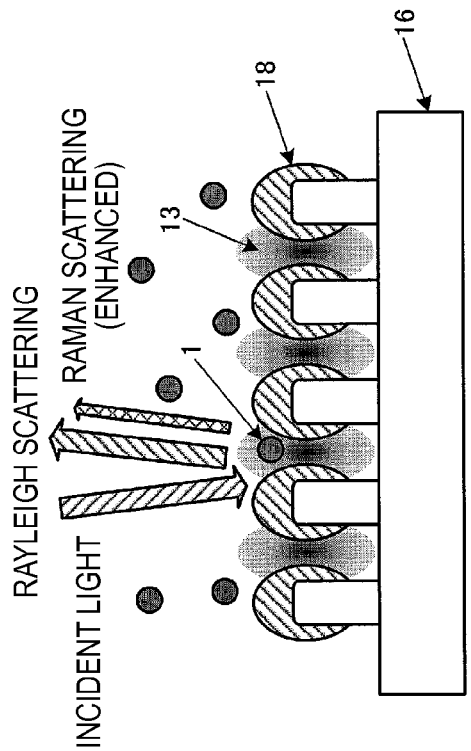
Figure 4D:
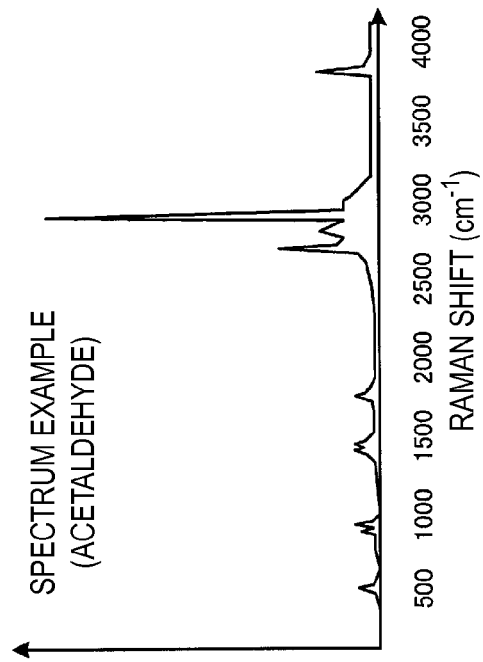

As shown in FIG. 4D, in a region where the incident light is incident, an enhanced electric field 13 is formed in a gap between the adjacent metal particles 18. In particular, as shown in FIG. 4C, when the metal particle 18 smaller than the wavelength λ of an incident light is irradiated with the incident light, the electric field of the incident light acts on free electrons present on the surface of the metal particle 18 to cause resonance. Due to this, electric dipoles are excited in the metal particle 18 by the free electrons, and an enhanced electric field 13 whose strength is higher than the electric field of the incident light is formed. This is also referred to as localized surface plasmon resonance (LSPR). This phenomenon is a phenomenon specific to the metal particle 18 having a convex portion with a size of 1 to 500 nm which is smaller than the wavelength of the incident light.

In this embodiment, localized surface plasmons and propagating surface plasmons can be used in combination. The propagating surface plasmons can be formed by a propagating structure formed by the metal layer 14. For example, as disclosed in Japanese Patent Application No. 2011-139526 (JP-A-2013-007614) applied by the present applicant, if the metal layer 14 has a lattice plane with irregularities, when a light is incident on the irregularities of the lattice, surface plasmons are generated. When the polarization direction of the incident light is orthogonalized to the groove direction of the lattice, the oscillation of electromagnetic waves is excited accompanying the oscillation of free electrons in the metal lattice. This oscillation of electromagnetic waves has an influence on the oscillation of free electrons, and therefore, a surface plasmon polariton which is a system in which both oscillations are combined is formed. Even if the metal layer 14 is smooth, the enhanced electric field 13 whose strength is higher than the electric field of the incident light can be formed (for example, Japanese Patent Application No. 2012-104401 applied by the present applicant).

3. Method for Producing Optical Device

FIGS. 5A to 5E show, for example, a method for producing an organic molecular layer 30A formed on a dielectric layer 16 as shown in FIG. 3A. In FIGS. 5A to 5E, only the dielectric layer 16 on which the organic molecular layer 30A is formed is shown. This dielectric layer 16 is formed on a metal layer 14 formed on a substrate 12 as shown in FIGS. 3A to 3C. However, the metal layer 14 may not be provided. Further, on the dielectric layer 16, silver (Ag) which is a material of the metal particle 18 is deposited to a thickness of 10 nm, whereby on the dielectric layer 16, a metal microstructure 20 is formed from an island structure in which the diameter of the silver metal particle 18 is about 70 nm, the height thereof is about 20 nm, and the distance between the metal particles 18 is about 5 nm.

Figure 5A:
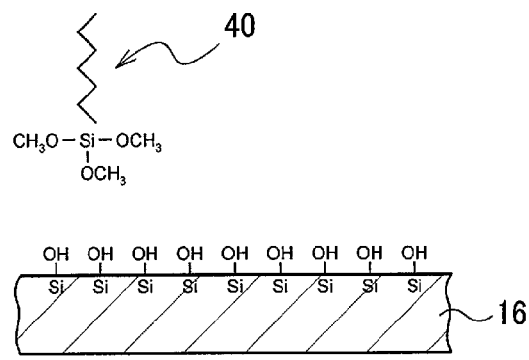
FIGS. 5A to 5E are views showing a method for producing an organic molecular layer formed on a dielectric layer.

First, as shown in FIG. 5A, on the dielectric layer 16, a layer of a first organic molecule 40 is grown by, for example, a vapor phase growth method. Here, when a backbone atom is represented by Si, a first organic group is represented by R1, a sterically hindered group is represented by Y1, and a first functional group to be attached to the substrate is represented by X1, the first organic molecule 40 is represented by the formula (1). As the backbone atom, any of Ti, Zr, and Al atoms can be used in place of Si.

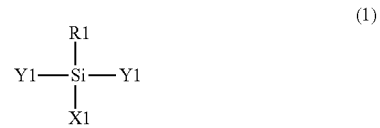

The sterically hindered group Y1 of the first organic molecule 40 shown in FIG. 5A is an alkoxy group (for example, a methoxy group $OCH_3$ having one carbon atom). In place of the methoxy group, any of an alkoxy group (having 2 to 10 carbon atoms), a phenoxy group, and a halogen group can be adopted as the sterically hindered group Y1.

Figure 6:
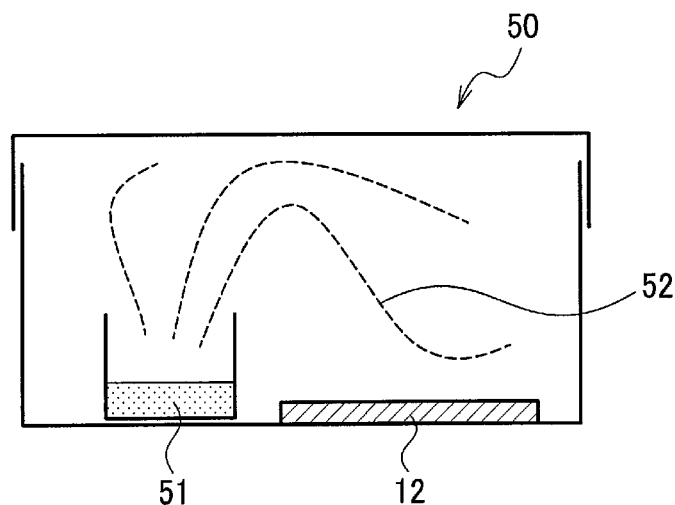
FIG. 6 is a view showing a vapor phase method for forming an organic molecular layer.

In the step shown in FIG. 5A, in an airtight container 50 shown in FIG. 6 in a glove box, 20 μL of a solution material 51 containing decyltrimethoxysilane (the group Y1 is a methoxy group ($OCH_3$) and the group R1 is an alkyl chain having 10 carbon atoms) as the first organic molecule 40 and a substrate 12 are placed, and heated for 1.5 hours in a thermoregulated bath at 100° C. Then, a gasified first organic molecule 52 is attached onto the dielectric layer 16 between the metal particles 18. In the step of forming the organic molecular layer, the method is not limited to the vapor phase growth method, and another method may be adopted.

Figure 5B:
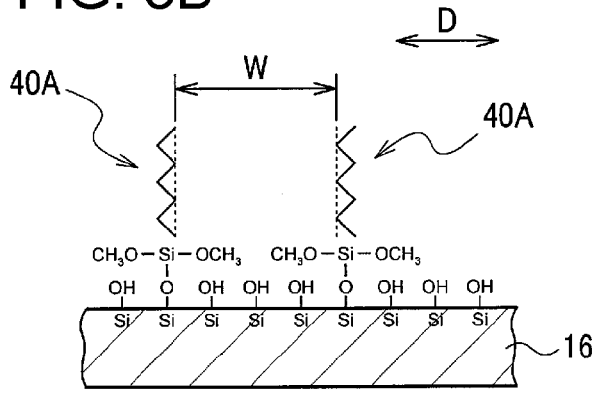

FIG. 5B shows a first organic molecule 40A after the first organic molecule 40 is attached to the dielectric layer (for example, $SiO_2$) 16. An alkoxy group (for example, a methoxy group $OCH_3$ having one carbon atom), which is the first functional group X1 to be attached to the dielectric layer 16 of the first organic molecule 40, is replaced by an oxygen atom by a condensation reaction when the group is attached to the dielectric layer 16. Also in the case where any of an alkoxy group (having 2 to 10 carbon atoms), a phenoxy group, a hydroxy group, and a halogen group is adopted as the first functional group X1 other than the methoxy group, the first functional group X1 is replaced by an oxygen atom by a condensation reaction when the group is attached to the dielectric layer 16.

Here, in the formation step shown in FIG. 5B, with respect to the two adjacent first organic molecules 40, 40 (see FIG. 5A) to be attached to the dielectric layer 16, an interval w in the arrangement direction D is regulated by the interference of the sterically hindered groups Y1 (see the formula (1)) protruding in the arrangement direction. Accordingly, the first organic molecule 40A is regularly arranged at an interval of w.

Figure 5C:
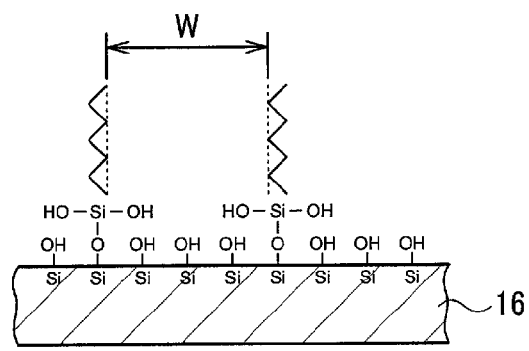

Subsequently, the substrate having the first organic molecule 40A is placed in a hermetically sealed container containing water, and heated to, for example, 80° C. for 1 hour. By doing this, the sterically hindered group Y1 in the first organic molecule 40A, which regulates the arrangement interval w in the arrangement direction, is hydrolyzed. That is, due to the following reaction: $Y1=OCH_3+H_2O \rightarrow OH+CH_3OH\uparrow$, the sterically hindered group Y1 is replaced by an OH group as shown in FIG. 5C.

Figure 5D:
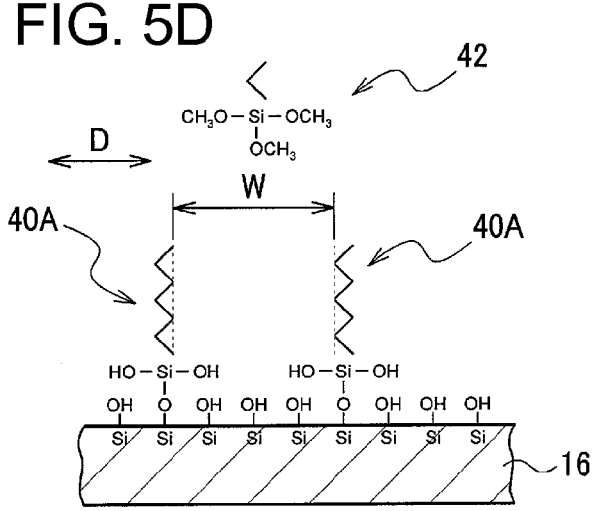

Subsequent, in the step shown in FIG. 5D, a second organic molecule 42 which is gasified in the same manner as the first organic molecule 40 is attached onto the dielectric layer 16 between the first organic molecules 40A.

Here, when a backbone atom is represented by Si, a second organic group is represented by R2, a second functional group to be attached to the substrate is represented by X2, and the remaining groups are represented by Y2 and Y3, the second organic molecule 42 is represented by the formula (2). As the backbone atom, any of Ti, Zr, and Al atoms can be used in place of Si.

(2)

Figure 5E:
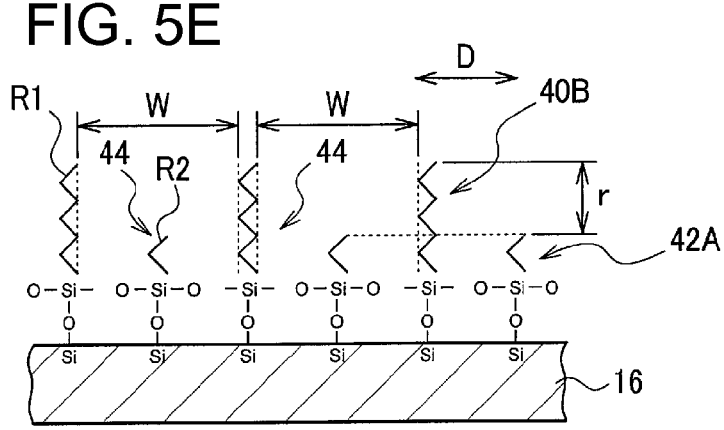

FIG. 5E shows the second organic molecule 42A after the second organic molecule 42 is attached to the dielectric layer (for example, $SiO_2$) 16. An alkoxy group (for example, a methoxy group $OCH_3$ having one carbon atom), which is the second functional group X2 to be attached to the dielectric layer 16 of the second organic molecule 42 is replaced by an oxygen atom by a condensation reaction occurring when the group is attached to the dielectric layer 16. Also in the case where any of an alkoxy group (having 2 to 10 carbon atoms), a phenoxy group (such as $OC_2H_5$), a hydroxy group (OH), and a halogen group (such as Cl) is adopted as the second functional group X2, the second functional group X2 is replaced by an oxygen atom by a condensation reaction occurring when the group is attached to the dielectric layer 16.

In FIG. 5E, the second organic molecule 42 enters between the two adjacent first organic molecules 40A in the arrangement direction D shown in FIG. 5D and is attached to the dielectric layer 16, whereby the second organic molecule 42A is formed. At this time, the sterically hindered group Y1 ($OCH_3$) of the first organic molecule 40 (40A) is present in FIG. 5B, however, in FIG. 5D, the sterically hindered group Y1 ($OCH_3$) has already been replaced by an OH group, and therefore is no longer an obstacle to the second organic molecule 42 entering between the two adjacent first organic molecules 40A in the arrangement direction D.

As shown in FIG. 5E, each of the groups Y2 and Y3 of the second organic molecule 42 (42A) and the OH group of the first organic molecule 40A are linked to each other by a condensation reaction and can be replaced by an oxygen atom. That is, the first organic molecule 40A and the second organic molecule 42A are linked to each other through an Si—O bond. The groups Y2 and Y3 of the second organic molecule 42 shown in FIG. 5D are each an alkoxy group $OCH_3$ (having one carbon atom). Also in the case where any of an alkoxy group (having 2 to 10 carbon atoms), a phenoxy group, a hydroxy group, and a halogen group is adopted as the groups Y2 and Y3 in place of this alkoxy group $OCH_3$, each of the groups Y2 and Y3 of the second organic molecule 42 is replaced by an oxygen atom by a condensation reaction when the group is linked to the OH group of the first organic molecule 40A. In FIG. 5E, the first organic molecule in which the OH group has been replaced by an oxygen atom is represented by 40B.

Each of the first organic group R1 of the first organic molecule 40 (40A, 40B) and the second organic group R2 of the second organic molecule 42 (42A) can have a linear, branched, or cyclic structure having one or more functional groups selected from the group consisting of an alkyl group, a vinyl group, an aryl group, a hydroxy group, an aldehyde group, a carbonyl group, a carboxy group, a nitro group, an amino group, a sulfo group, an ether bond, an ester bond, an amide bond, a cyano group, an imino group, a cycloalkyl group, an alkenyl group, an alkynyl group, an epoxy group, a mercapto group, and a halogen group.

Here, as the first organic group R1 and the second organic group R2, those having a different chain length as shown in FIG. 5E are selected from the above-described functional groups. Even in the case of the functional groups of the same type, some functional groups have a different chain length since, for example, the number of carbon atoms is different, and therefore, the first organic group R1 and the second organic group R2 may be functional groups of the same type as long as the chain lengths thereof are different.

In this manner, according to the structure shown in FIG. 5E, the first organic molecule 40B linked to the second organic molecule 42A is regularly arranged at an arrangement interval of w in the arrangement direction D, and the second organic molecule 42A is arranged between the two adjacent first organic molecules 40B in the arrangement direction D. Accordingly, a capture space (capture region) 44 having a depth corresponding to a chain length difference r between the first organic group R1 and the second organic group R2 and having a width corresponding to the arrangement interval w of the first organic molecule 40B is regularly formed. In FIGS. 5A to 5E, only a one-dimensional arrangement direction D is shown, however, the first organic molecule 40B and the second organic molecule 42A can be arranged two-dimensionally in a checkered pattern in arrangement directions intersecting, for example, orthogonal to the arrangement direction D.

FIGS. 5A to 5D are views explaining the method for producing the organic molecular layer 30A shown in FIG. 3A, however, the organic molecular layer 30B to be formed on the metal particle 18 shown in FIG. 3B or 3C can also be formed in the same manner. A difference with the method shown in FIGS. 5A to 5D is the functional groups X1 and X2, each of which forms a bond when the first and second organic molecules 40 and 42 are attached to the metal particle 18.

When the organic molecular layer 30B is formed on the metal particle 18, as the first functional group X1 and the second functional group X2, any of a thiol group (R—SH), a thioisocyanide group (R—S—S—R), and an isocyanide group (R—CN) can be adopted. If the first functional group X1 and the second functional group X2 are each a thiol group or a thioisocyanide group, an S-metal bond is formed when each group is attached to the metal particle 18, and if the first functional group X1 and the second functional group X2 are each an isocyanide group, an NC-metal bond is formed when each group is attached to the metal particle 18.

4. Optical Device Having Capture Space Matched with Size of Target Molecule

Figure 7A:
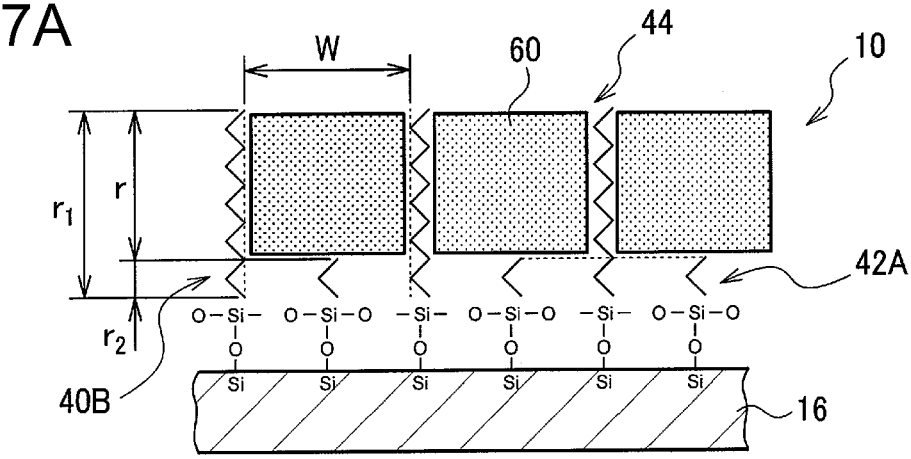
FIGS. 7A and 7B are views for explaining the size of a capture space of an organic molecular layer and the size of a target molecule.
Figure 7B:
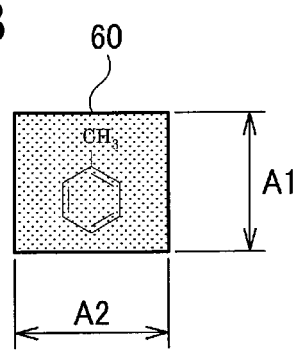

FIGS. 7A and 7B are views for explaining the size of a capture space 44 of the organic molecular layer 30A and the size of a target molecule 60. Here, the size of the capture space 44 capable of capturing the target molecule 60 as shown in FIG. 7A is examined. The capture space 44 is defined by a chain length difference r (=r1−r2) between the chain length r1 of the first organic group R1 of the first organic molecule 40B and the chain length r2 of the second organic group R2 of the second organic molecule 42A and the arrangement interval w of the first organic molecule 40B having a long chain length. Subsequently, the size of the target molecule 60 is defined. In FIG. 7B, the lengths of two axes defining the maximum projected area among the projected areas in three orthogonal axial directions of the target molecule 60 are represented by A1 and A2 (with the proviso that A1 A2).

Figure 8:
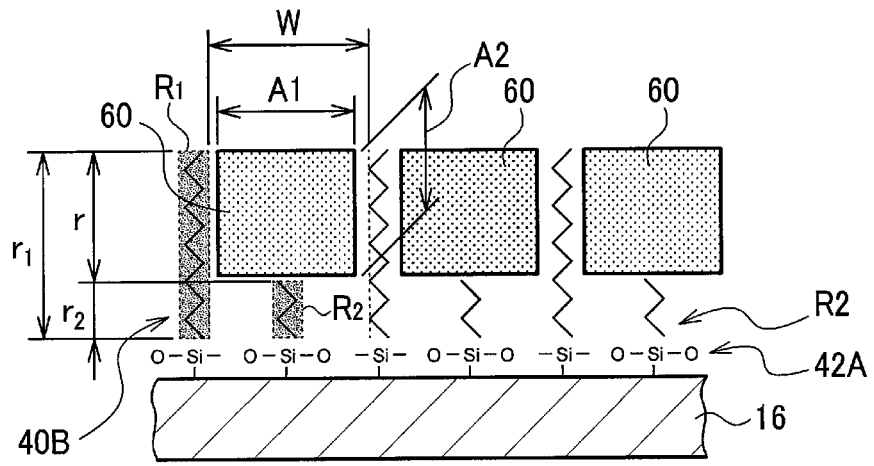
FIG. 8 is a view showing a first method for setting the size of a capture space conforming to the size of a target molecule.
Figure 9:
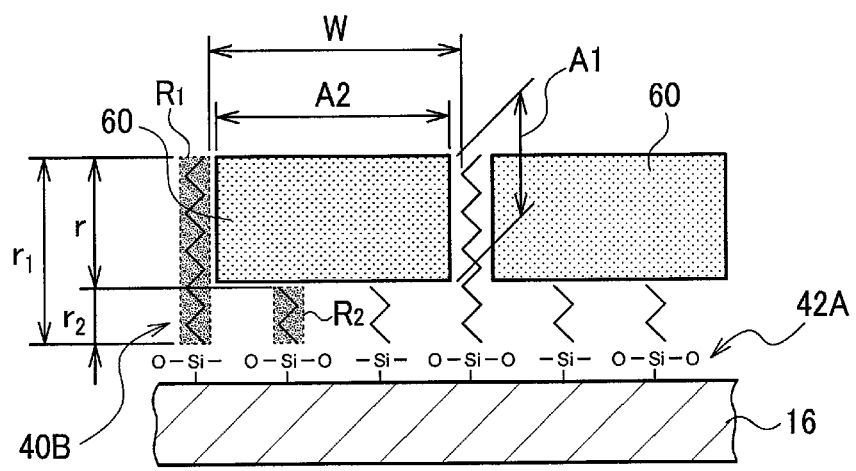
FIG. 9 is a view showing a second method for setting the size of a capture space conforming to the size of a target molecule.

The size of the capture space 44 conforming to the size of the target molecule 60 is defined in two ways as shown in FIGS. 8 and 9. In FIG. 8, the size of the capture space 44 is defined according to the following formulae: $A1<w$ and $A2≤r$. According to this, the entire target molecule 60 enters in the capture space 44. As a result, through the organic group R2 of the second organic molecule 42A located on the bottom surface of the capture space 44 and the organic group R1 of the first organic molecule 40B located on the side surface of the capture space 44, the target molecule 60 can be held by multipoint adsorption.

In consideration of the upper limit of the size of the capture space 44, the following formula can be established: $A1 < w \leq 2 \times A1$. According to this, two or more target molecules 60 do not enter in the one capture space 44 in the width direction, and the density of the capture space 44 can be increased by decreasing the arrangement pitch of the capture space 44. As a result, the number of the target molecules 60 to be captured in the capture spaces 44 can be increased, and thus, the SERS signal intensity can be increased. As for the depth of the capture space 44, for example, the following formula can be established: $A2 \leq r \leq 2 \times A2$. According to this, particularly in the case where $A1 < A2$, the depth r of the vertically long capture space 44 is not too large for the size of the target molecule 60, and thus, it becomes easy for the target molecule 60 to reach the bottom surface of the capture space 44.

As described above, by allowing the size of the capture space 44 to conform to the size of the target molecule 60, it becomes possible to select the target molecule 60 by the capture space 44. That is, a noise molecule having a size larger than the target molecule 60 is not captured by the capture space 44. In this manner, since the capture space 44 is not occupied by a noise molecule, the detection signal level for the target molecule 60 can be increased.

In the case where the size of the target molecule satisfies the following formula: $A1 < A2$ in the same manner as in FIG. 8, the size of the capture space 44 shown in FIG. 9 may be adopted in place of FIG. 8. In FIG. 9, the size of the capture space 44 is defined by the following formulae: $A2 < w$ and $A1 \leq r$. Also in this case, the entire target molecule 60 enters in the capture space 44 in a horizontally long state. As a result, through the organic group R2 of the second organic molecule 42A located on the bottom surface of the capture space 44 and the organic group R1 of the first organic molecule 40B located on the side surface of the capture space 44, the target molecule 60 can be held by multipoint adsorption.

When the upper limit of the size of the capture space 44 is defined with reference to FIG. 9 in the same manner as FIG. 8, in the case where $A1 \leq A2$, the following formulae can be established: $A2 < w \leq 2 \times A2$; and $A1 \leq r \leq 2 \times A1$. According to this, the length A1 of the target molecule 60 is within the depth r of the capture space 44, and the other length A2 is within the width w of the capture space 44, and thus, the target molecule 60 can be adsorbed in the capture space 44 conforming to the size of the target molecule 60. Also in this case, the detection signal level for the target molecule can be increased in the same manner as FIG. 8. However, the arrangement density of the capture space 44 and the selectivity for the target molecule 60 of the capture space 44 are lower than in the case shown in FIG. 8.

Figure 10A:
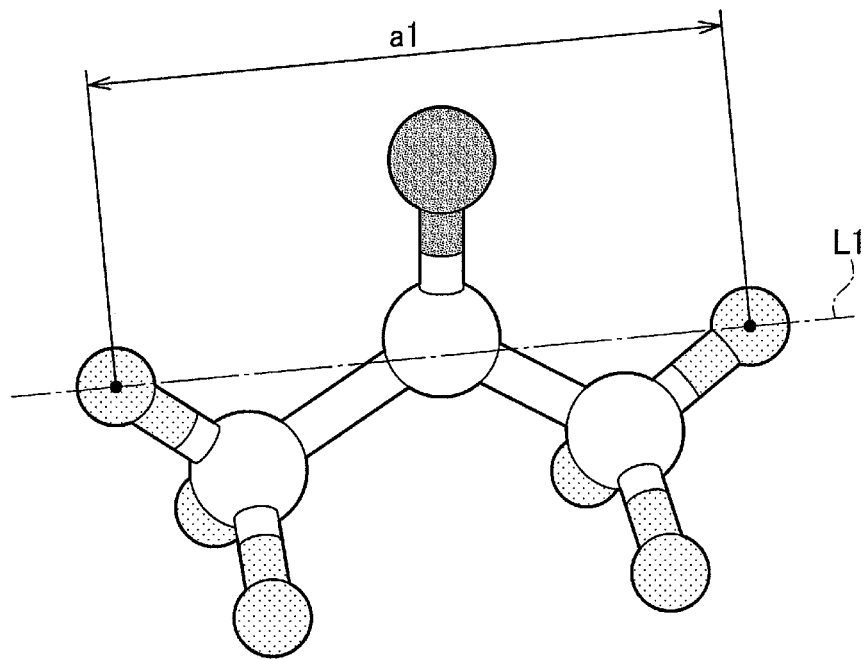
FIGS. 10A and 10B are views showing the lengths a1 and a2 of a target molecule (acetone), respectively.
Figure 10B:
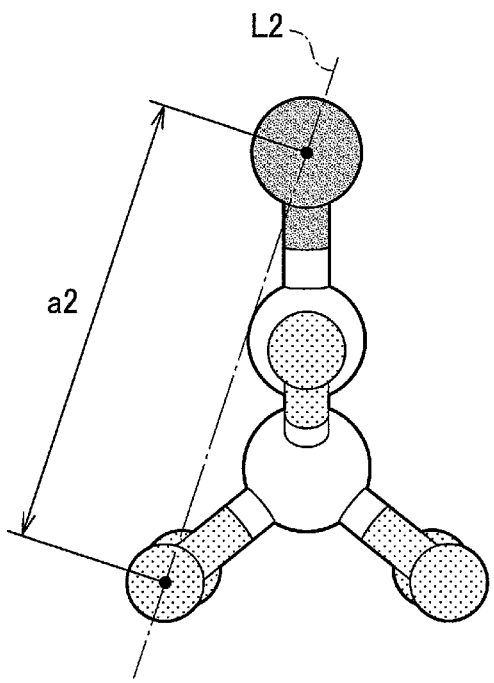

Here, in order to determine the lengths A1 and A2 in two orthogonal axial directions shown in FIG. 7B, reference can be made to the lengths a1 and a2 of the target molecule 60 shown in FIGS. 10A and 10B. Incidentally, as the bond distance and the bond angle of the target molecule 60, values obtained according to Kagaku Benran Kiso-hen II (Chemical Handbook, Fundamentals II), revised 2nd ed., edited by The Chemical Society of Japan (Maruzen) can be used. In the molecular structure of the target molecule 60, for example, acetone, as shown in FIG. 10A, a straight line connecting two atoms located farthest from each other in the molecule is defined as a first axis L1. A distance between the centers of the two atoms located farthest from each other on the first axis L1 is represented by a1. Subsequently, as shown in FIG. 10B, a straight line connecting two atoms located farthest from each other in an orthogonal projection on a surface orthogonal to the first axis L1 is defined as a second axis L2, and a distance between the centers of the two atoms located farthest from each other on the second axis L2 is represented by a2. In the case of acetone, a1=0.43 nm, and a2=0.28 nm.

Figure 11A:
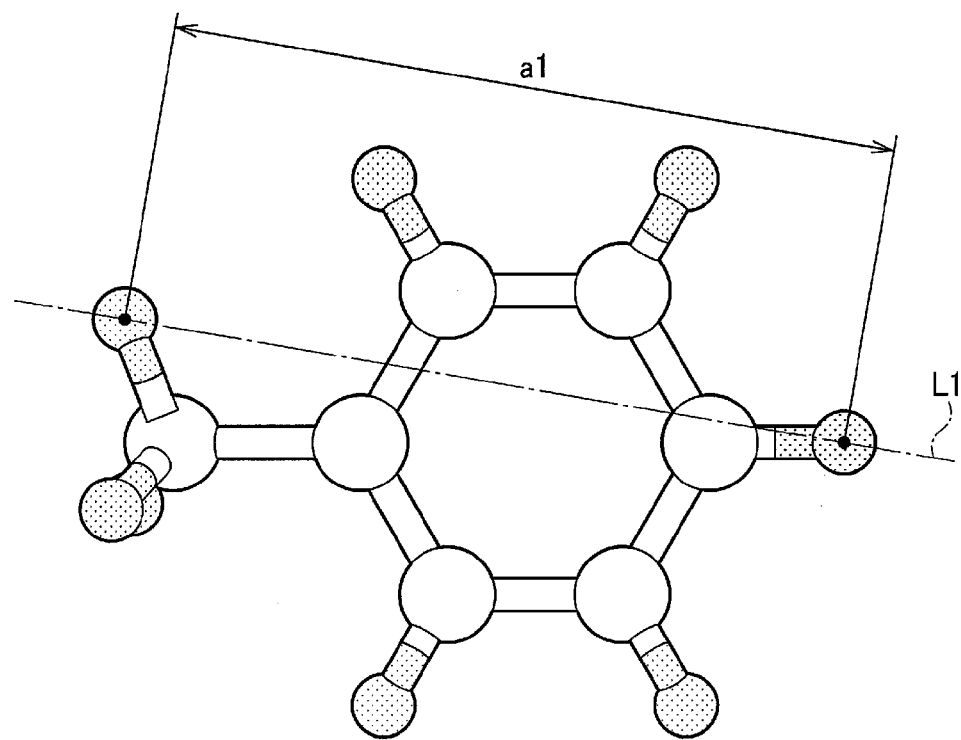
FIGS. 11A and 11B are views showing the lengths a1 and a2 of a target molecule (toluene), respectively.
Figure 11B:
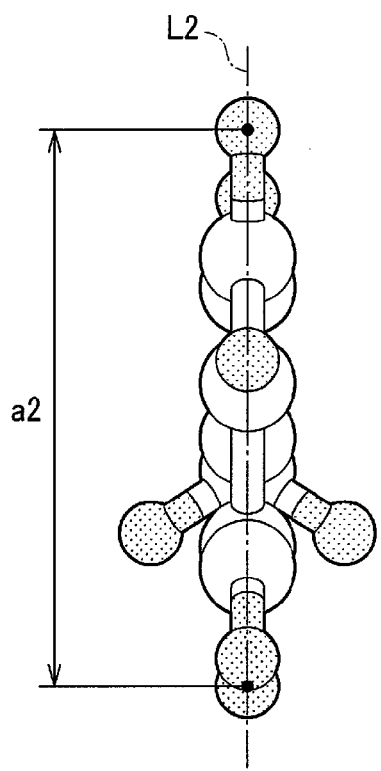

FIGS. 11A and 11B show a case of toluene. The length a1 on the first axis L1 and the length a2 on the second axis L2 as determined in the same manner as FIGS. 10A and 10B are as follows: a1=0.59 nm, and a2=0.47 nm.

The first axis L1 and the second axis L2 determined from FIGS. 10A and 10B and FIGS. 11A and 11B are not always orthogonal to each other, and therefore, the above-described lengths a1 and a2 do not coincide with the lengths A1 and A2 shown in FIG. 7B, however, in order to obtain the lengths A1 and A2, reference can be made to the lengths a1 and a2.

FIGS. 12A and 12B, FIGS. 13A and 13B, and FIGS. 14A and 14B show the lengths A1 and A2 (with the proviso that $A1 \leq A2$) of toluene, acetone, and isoprene determined as described above and the capture spaces 44 conforming thereto, respectively.

FIG. 15 shows the width w of the capture space 44 adjusted by the group Y1 of the first organic molecule 40. The width w of the capture space 44 may be determined in accordance with the size of the target molecule 60. For example, since the length A1 of a toluene molecule is about 0.5 nm, it is preferred to use a first organic molecule 40 having $OCH_2CH_3$ as the group Y1 so that the capture space 44 has a size larger than 0.5 nm. Further, in the case of acetone, since the length A2 is about 0.45 nm, it is preferred to select a first organic molecule 40 having $OCH_3$ or $OCH_2CH_3$ as the group Y1. In the case of isoprene, since the length A1 is about 0.4 nm, it is preferred to select a first organic molecule 40 having $OCH_3$ or $OCH_2CH_3$ as the group Y1.

The depth r of the capture space 44 is determined by a chain length difference (r1−r2) between the chain length r1 of the first organic group R1 and the chain length r2 of the second organic group R2, and in FIG. 16, Examples 1 to 3 are shown. The chain lengths r1 and r2 of the organic groups R1 and R2 in FIG. 16 can be determined from the bond distance and the bond angle in the same manner as the size of the target molecule 60 described above. Since the length A2 of a toluene molecule is about 0.6 nm, it is considered that the use of the combination of Example 2 in FIG. 16 is suitable. Further, in the case of acetone, since the length A1 is about 0.3 nm, it is preferred to use Example 3 in FIG. 16. In the case of isoprene, since the length A2 is about 0.5 nm, it is preferred to use Example 2 in FIG. 16.

By using the optical device 10 produced as described above, acetone gas molecules are exposed, and the results obtained by SERS detection are shown in FIG. 17. By using a laser at 632.8 nm with a power of 0.5 mW as an excitation light, the measurement was performed by setting the exposure time to 30 seconds. By way of comparison, the experimental results obtained using a device before forming the organic molecular layer (SAM), and a device in which only one type of SAM1 (the first organic molecule) was formed are also shown in FIG. 17. The method for producing the optical device in which only SAM1 was formed was performed according to the procedures of the production method of this embodiment shown in FIGS. 5A to 5E with the proviso that SAM1 was used in place of SAM2 (the second organic molecule) in FIGS. 5D and 5E.

In FIG. 17, the SERS peak intensity (counts) of a signal at 787 $cm^{-1}$ specific to acetone in the case of using the optical device of this embodiment is larger than in the case of using a substrate in which an SAM was not formed and a substrate in which only SAM1 was formed. By using the optical device 10 produced according to the method of this embodiment, the detection capability as an SERS sensor can be improved.

5. Overall Structure of Detection Apparatus

Figure 18:
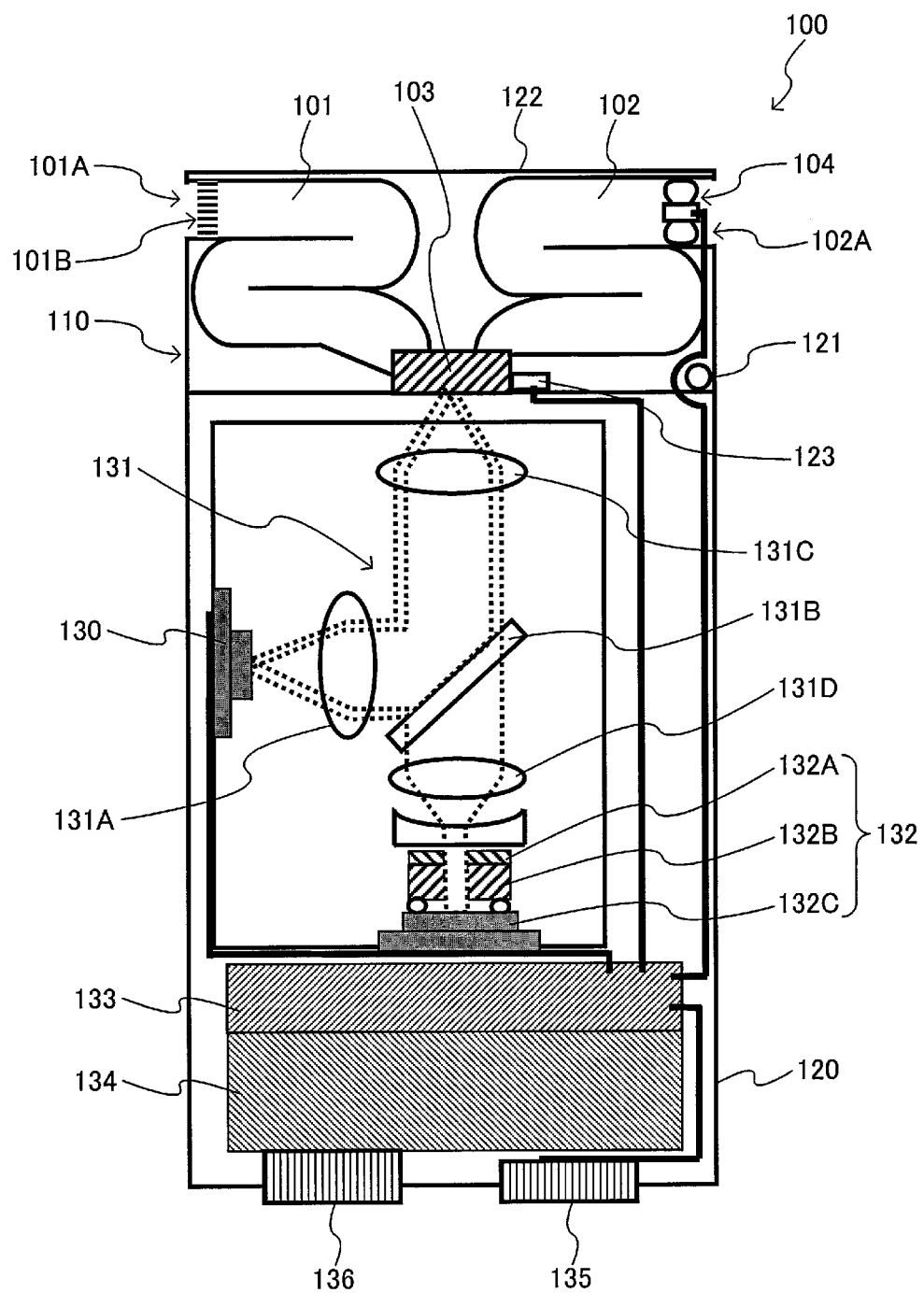
FIG. 18 is a view showing the overall structure of a detection apparatus according to an embodiment of the invention.

Next, the overall structure of a detection apparatus will be described. FIG. 18 shows a specific structural example of a detection apparatus of this embodiment. A detection apparatus 100 shown in FIG. 18 includes a sample supply channel 101 having a suction port 101A and a dust removal filter 101B, a sample discharge channel 102 having a discharge port 102A, and an optical device unit 110 provided with an optical device (sensor chip) 103 having a structure shown in FIG. 3, and the like. On the optical device 103, a light is incident. A housing 120 of the detection apparatus 100 includes a sensor cover 122 which can be opened and closed by a hinge section 121. The optical device unit 110 is detachably mounted on the housing 120 in the sensor cover 122. The mounted or unmounted state of the optical device unit 110 can be detected by a sensor detector 123.

The sample supply channel 101 and the sample discharge channel 102 are each formed into a winding shape and therefore have a structure such that an outside light hardly enters.

Incidentally, a consideration is given to the shapes of the channels through which a fluid sample is sucked or discharged so that a light from outside does not enter the sensor and the fluid resistance to the fluid sample is decreased, respectively. By adopting a structure in which an outside light does not enter the optical device 103, a noise light other than a Raman scattered light does not enter, and thus the S/N ratio of a signal is improved. Also for the constituent material of the channel as well as the shape of the channel, it is necessary to select a material, a color, and a surface profile so that the light is hardly reflected. Further, by decreasing the fluid resistance to the fluid sample, the fluid sample in the vicinity of this apparatus can be collected much, and highly sensitive detection can be achieved. As the shape of the channel, by adopting a smooth shape in which an angular portion is eliminated as much as possible, accumulation of the sample at an angular portion does not occur. It is also necessary to select a fan or a pump capable of producing a static pressure and an air flow appropriate to the channel resistance as a negative pressure generation section 104 provided in the fluid discharge channel 102.

In the housing 120, a light source 130, an optical system. 131, a light detection section 132, a signal processing control section 133, and an electric power supply section 134 are provided.

In FIG. 18, the light source 130 is, for example, a laser, and from the viewpoint of reduction in size, it is preferred to use a vertical-cavity surface-emitting laser, but the light source is not limited thereto.

The light from the light source 130 is converted to a parallel light by a collimator lens 131A which constitutes the optical system 131. It is also possible to convert the parallel light to a linearly polarized light by providing a polarization control element downstream the collimator lens 131A. However, the polarization control element can be omitted if a light containing a linearly polarized light can be emitted by adopting, for example, a surface-emitting laser as the light source 130.

The light converted to the parallel light by the collimator lens 131A is guided toward the optical device 103 by a half mirror (dichroic mirror) 131B, and collected by an objective lens 131C, and then, incident on the optical device 103. A Rayleigh scattered light and a Raman scattered light from the optical device 103 pass through the objective lens 131C and are guided toward the light detection section 132 by the half mirror 131B.

The Rayleigh scattered light and the Raman scattered light from the optical device 103 are collected by a collecting lens 131D and incident on the light detection section 132. In the light detection section 132, first, the lights arrive at a light filter 132A. By the light filter 132A (for example, a notch filter), the Raman scattered light is extracted. This Raman scattered light further passes through a spectroscope 132B and is then received by the light-receiving element 132C. The spectroscope 132B is formed from an etalon or the like utilizing, for example, Fabry-Perot resonance, and can make a pass wavelength band variable. The wavelength of the light passing through the spectroscope 132B can be controlled (selected) by the signal processing control section 133. By the light-receiving element 132C, a Raman spectrum specific to a target molecule 1 is obtained, and by collating the obtained Raman spectrum with previously held data, the target molecule 1 can be identified.

The electric power supply section 134 supplies electric power from a power supply connection section 135 to the light source 130, the light detection section 132, the signal processing control section 133, the fan 104, and the like. The electric power supply section 134 can be composed of, for example, a secondary battery, and may also be composed of a primary battery, an AC adapter, or the like. A communication connection section 136 is connected to the signal processing control section 133, and transmits data, control signals, and the like to the signal processing control section 133.

In the example shown in FIG. 18, the signal processing control section 133 can send a command to the light detection section 132, the fan 104, and the like other than the light source 130 shown in FIG. 18. Further, the signal processing control section 133 can perform a spectroscopic analysis using the Raman spectrum, and the signal processing control section 133 can also identify the target molecule 1. Incidentally, the signal processing control section 133 can transmit the detection results obtained by the Raman scattered light, the spectroscopic analysis results obtained by the Raman spectrum, and the like to, for example, an external apparatus (not shown) connected to the communication connection section 136.

Figure 19:
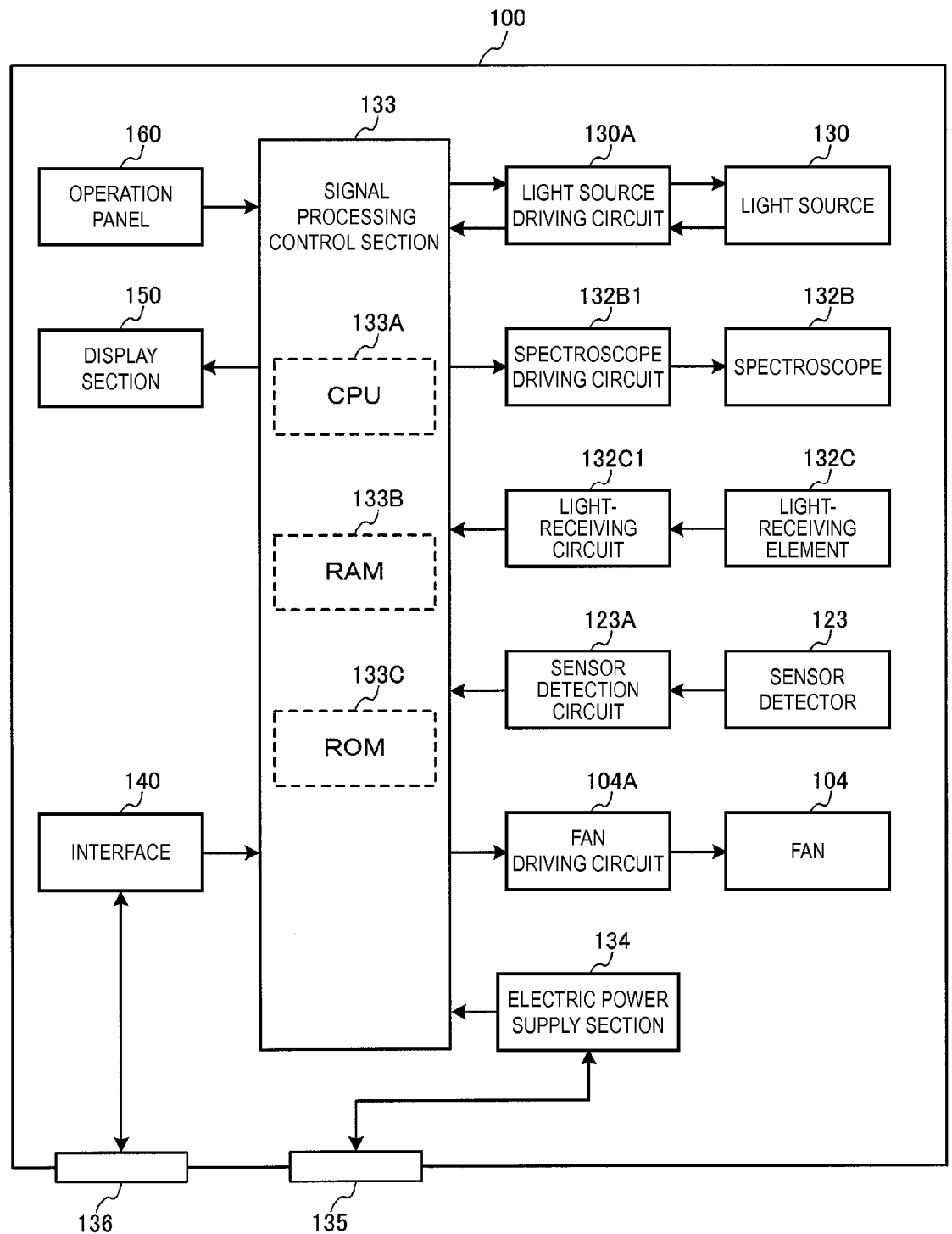
FIG. 19 is a block diagram of a control system of the detection apparatus shown in FIG. 18.

FIG. 19 is a block diagram of a control system of the detection apparatus 100 shown in FIG. 18. The detection apparatus 100 can further include, for example, an interface 140, a display section 150, an operation panel 160, and the like. Further, the signal processing control section 133 shown in FIG. 19 can include a central processing unit (CPU) 133A as the control section, a random access memory (RAM) 133B, a read only memory (ROM) 133C, and the like.

Further, the detection apparatus 100 can include a light source driving circuit 130A, a spectroscope driving circuit 132B1, a sensor detection circuit 123A, a light-receiving circuit 132C1, a fan driving circuit 104A, and the like, which drive the respective members shown in FIG. 18.

An electronic apparatus including: the detection apparatus 100; a calculation section (not shown) which calculates health or medical information on the basis of the detection results from the detection apparatus 100; a display section (not shown) which displays the health or medical information; and a storage section (not shown) which stores the health or medical information is useful for medical diagnoses, tests for foods and beverages, etc. For example, by using this electronic apparatus, the concentration of a very small amount of acetone contained in human breath is detected, the amount of fat combustion is displayed, and the relationship with the amount of exercise and the like are ascertained. In this manner, this electronic apparatus can be utilized for prevention of adult diseases, etc.

While the embodiments have been described in detail in the above description, it could be easily understood by those skilled in the art that various modifications thereof can be made without departing in substance from the novel matter and effects of the invention. Therefore, such modifications all fall within the scope of the invention. For example, in the specification or the drawings, a term which is described at least once together with a different term having a broader meaning or the same meaning can be replaced with the different term in any parts of the specification or the drawings. Further, the structures and operations of the optical device and the detection apparatus are not limited to those described in the embodiments, and various modifications can be made.

The entire disclosure of Japanese Patent Application No. 2012-272042, filed Dec. 13, 2012 is expressly incorporated by reference herein.

What is claimed is:

1. An optical device comprising:
    a substrate having a dielectric layer and metal particles; and
    an organic molecular layer formed by self-assembly on at least either the surface of the dielectric layer or the surfaces of the metal particles, wherein
    in the organic molecular layer, a first organic molecule and a second organic molecule are alternately arranged in a first direction,
    the chain length of an organic group of the first organic molecule and the chain length of an organic group of the second organic molecule are different from each other,
    the organic molecular layer has a capture region in which a given substance is captured on the surface thereof,
    the capture region is defined by a chain length difference between the organic group of the first organic molecule and the organic group of the second organic molecule and the arrangement interval of the first organic molecule having a longer chain length than the second organic molecule, and
    the self-assembly occurs such that the organic molecular layer, in which the molecules have the same orientation, is formed on the surface by an interaction between the first organic molecule and the second organic molecule adsorbed on the surface in a solution or a vapor.

2. The optical device according to claim 1, wherein
    when the chain length difference between the organic group of the first organic molecule and the organic group of the second organic molecule is represented by r, the arrangement interval of the first organic molecule is represented by w, and the lengths of two axes defining the maximum area among the projected areas in three orthogonal axial directions of the given substance are represented by A1 and A2 (A1≤A2), r, w, A1, and A2 satisfy the following formulae: A1<w≤2×A1; and A2≤r≤2×A2.

3. The optical device according to claim 2, wherein
    when the length of a first axis connecting two atoms located farthest from each other in the given substance is represented by a1, and the length of a second axis connecting two atoms located farthest from each other in an orthogonal projection of the given substance on a surface orthogonal to the first axis is represented by a2, the length A1 and the length A2 are defined on the basis of the length a1 of the first axis and the length a2 of the second axis, respectively.

4. A detection apparatus comprising:
    a light source;
    the optical device according to claim 3, on which a light from the light source is incident; and
    a light detector which detects a light emitted from the optical device.

5. A detection apparatus comprising:
    a light source;
    the optical device according to claim 2, on which a light from the light source is incident; and
    a light detector which detects a light emitted from the optical device.

6. An electronic apparatus comprising:
    the detection apparatus according to claim 5;
    a calculation section which calculates health or medical information on the basis of the detection information from the detection apparatus;
    a storage section which stores the health or medical information; and
    a display section which displays the health or medical information.

7. The optical device according to claim 1, wherein
    when the chain length difference between the organic group of the first organic molecule and the organic group of the second organic molecule is represented by r, the arrangement interval of the first organic molecule is represented by w, and the lengths of two axes defining the maximum area among the projected areas in three orthogonal axial directions of the given substance are represented by A1 and A2 (A1≤A2), r, w, A1, and A2 satisfy the following formulae: A2<w≤2×A2; and A1≤r≤2×A1.

8. A detection apparatus comprising:
    a light source;
    the optical device according to claim 7, on which a light from the light source is incident; and
    a light detector which detects a light emitted from the optical device.

9. An electronic apparatus comprising:
    the detection apparatus according to claim 8;
    a calculation section which calculates health or medical information on the basis of the detection information from the detection apparatus;
    a storage section which stores the health or medical information; and
    a display section which displays the health or medical information.

10. A detection apparatus comprising:
    a light source;
    the optical device according to claim 1, on which a light from the light source is incident; and
    a light detector which detects a light emitted from the optical device.

11. An electronic apparatus comprising:
    the detection apparatus according to claim 10;
    a calculation section which calculates health or medical information on the basis of the detection information from the detection apparatus;
    a storage section which stores the health or medical information; and
    a display section which displays the health or medical information.

12. An optical device comprising:
    a substrate having a dielectric layer and metal particles; and
    an organic molecular layer formed by self-assembly on at least either the surface of the dielectric layer or the surfaces of the metal particles, wherein
    in the organic molecular layer, a first organic molecule and a second organic molecule are arranged in a checkered pattern, and the chain length of an organic group of the first organic molecule and the chain length of an organic group of the second organic molecule are different from each other.

13. A method for producing an optical device comprising:
forming an organic molecular layer on at least either the surface of a dielectric layer or the surfaces of metal particles formed on a substrate by self-assembling a first organic molecule having a first organic group in an arrangement direction so as to maintain a predetermined interval;
removing a sterically hindered group in the first organic molecule which regulates the interval by hydrolysis; and
forming an organic molecular layer by self-assembling a second organic molecule having a second organic group with a different chain length from the first organic group between the adjacent first organic molecules on the surface,
wherein when a backbone atom is represented by Si, the first organic group is represented by R1, the sterically hindered group is represented by Y1, and a first functional group to be attached to the substrate is represented by X1, the first organic molecule is represented by the formula (1):

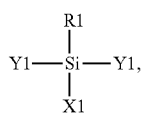
(1)

and
the sterically hindered group Y1 is any of an alkoxy group (having 1 to 10 carbon atoms), a phenoxy group, and a halogen group, and is replaced by an OH group by hydrolysis.

14. The method for producing an optical device according to claim 13, wherein
when a backbone atom is represented by Si, the second organic group is represented by R2, a second functional group to be attached to the substrate is represented by X2, and the remaining groups are represented by Y2 and Y3, the second organic molecule is represented by the formula (2):

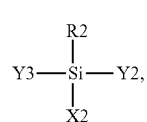
(2)

and
the group Y2 and the group Y3 each are any of an alkoxy group (having 1 to 10 carbon atoms), a phenoxy group, a hydroxy group, and a halogen group.

15. The method for producing an optical device according to claim 14, wherein
the first organic group R1 and the second organic group R2 each have a linear, branched, or cyclic structure having one or more functional groups selected from the group consisting of an alkyl group, a vinyl group, an aryl group, a hydroxy group, an aldehyde group, a carbonyl group, a carboxy group, a nitro group, an amino group, a sulfo group, an ether bond, an ester bond, an amide bond, a cyano group, an imino group, a cycloalkyl group, an alkenyl group, an alkynyl group, an epoxy group, a mercapto group, and a halogen group.

16. The method for producing an optical device according to claim 14, wherein
when the first organic molecule and the second organic molecule are formed on the dielectric layer, the first functional group X1 and the second functional group X2 are each any of an alkoxy group (having 1 to 10 carbon atoms), a phenoxy group, a hydroxy group, and a halogen group.

17. The method for producing an optical device according to claim 14, wherein
when the first organic molecule and the second organic molecule are formed on a plurality of the metal particles, the first functional group X1 and the second functional group X2 are each any of a thiol group, a thioisocyanide group, and an isocyanide group.

18. The method for producing an optical device according to claim 13, wherein
as the backbone atom, any of Ti, Zr, and Al atoms is used in place of Si.

* * * * *